(12) United States Patent
Son et al.

(10) Patent No.: US 9,078,851 B2
(45) Date of Patent: Jul. 14, 2015

(54) COMPOSITION FOR PREVENTING OR TREATING A SPINAL CORD INJURY

(75) Inventors: Young Sook Son, Seoul (KR); Mei Hua Jiang, Yongin-si (KR)

(73) Assignee: UNIVERSITY-INDUSTRY COOPERATION GROUP OF KYUNG HEE, Yongin-Si (KR)

(*) Notice: Subject to any disclaimer, the term of this patent is extended or adjusted under 35 U.S.C. 154(b) by 262 days.

(21) Appl. No.: 13/390,892

(22) PCT Filed: Aug. 17, 2010

(86) PCT No.: PCT/KR2010/005419
§ 371 (c)(1),
(2), (4) Date: May 11, 2012

(87) PCT Pub. No.: WO2011/021832
PCT Pub. Date: Feb. 24, 2011

(65) Prior Publication Data
US 2012/0225821 A1 Sep. 6, 2012

(30) Foreign Application Priority Data

Aug. 17, 2009 (KR) ........................ 10-2009-0075880

(51) Int. Cl.
*A01N 37/18* (2006.01)
*A61K 38/00* (2006.01)
*A61K 38/10* (2006.01)

(52) U.S. Cl.
CPC ...................................... *A61K 38/10* (2013.01)

(58) Field of Classification Search
None
See application file for complete search history.

(56) References Cited

U.S. PATENT DOCUMENTS

| 2003/0165541 A1 | 9/2003 | Donovan ................... 424/236.1 |
| 2007/0207209 A1 | 9/2007 | Murphy et al. ............... 424/484 |

FOREIGN PATENT DOCUMENTS

WO 2009/017655 A2 2/2009

OTHER PUBLICATIONS

Deguchi et al., "Substance P immunoreactivity in the enteric nervous system in Rett syndrome," *Brain & Development* 23:S127-S132, 2001.
Donkin et al., "Substance P in traumatic brain injury," *Progress in Brain Research* 161:97-109, 2007.
Huston et al., "Sequence-specific effects of neurokinin substance P on memory, reinforcement, and brain dopamine activity," *Psychopharmacology* 112:147-162, 1993.
International Search Report, for International Application No. PCT/KR2010/005419, mailed May 23, 2011, 9 pages.
Naftchi et al., "Prevention of Damage in Acute Spinal Cord Injury by Peptides and Pharmacologic Agents," *Peptides* 3:235-247, 1982.
Nomura et al., "Decrease of substance P in the parabrachial nucleus of multiple system atrophy," *Autonomic Neuroscience: Basic and Clinical* 92:86-91, 2001.
Hamilton, "Colony-Stimulating Factors in Inflammation and Autoimmunity," *Nature Reviews Immunology* 8(7):533-544, Jul. 2008, 12 pages.
Rueff et al., "Nerve Growth Factor and Inflammatory Pain," Technical Corner from *IASP Newsletter*, Jan./Feb. 1996, 5 pages.
Villarreal et al., "Inflammation: Acute," *Encyclopedia of Life Sciences*, 2001, 8 pages.
Wang et al., "Role of TGFβ-Mediated Inflammation in Cutaneous Wound Healing," *Journal of Investigative Dermatology Symposium Proceedings* 11:112-117, 2006, 6 pages.
Zittermann et al., "Basic Fibroblast Growth Factor (bFGF, FGF-2) Potentiates Leukocyte Recruitment to Inflammation by Enhancing Endothelial Adhesion Molecule Expression," *American Journal of Pathology* 168(3):835-846, Mar. 2006, 12 pages.

*Primary Examiner* — Olga N Chernyshev
(74) *Attorney, Agent, or Firm* — Seed IP Law Group PLLC

(57) ABSTRACT

The present invention relates to a novel use of substance P. The substance P of the present invention exhibits effects of decreasing microglia activity, decreasing proinflammatory cytokines, inhibiting apoptosis, etc. The substance P of the present invention effectively treats degenerative central nervous system diseases or disorders such as a spinal cord injury caused by a traumatic injury (flexion injury, vertical compression injury, hyperextension injury, flexion-rotation injury) and by a non-traumatic injury (vascular dysfunction, arthritis, or degenerative arthritis), Parkinson's disease, Alzheimer's disease, amyotrophic lateral sclerosis, Huntington's disease, depressive disorder, epilepsy, etc.

2 Claims, 12 Drawing Sheets

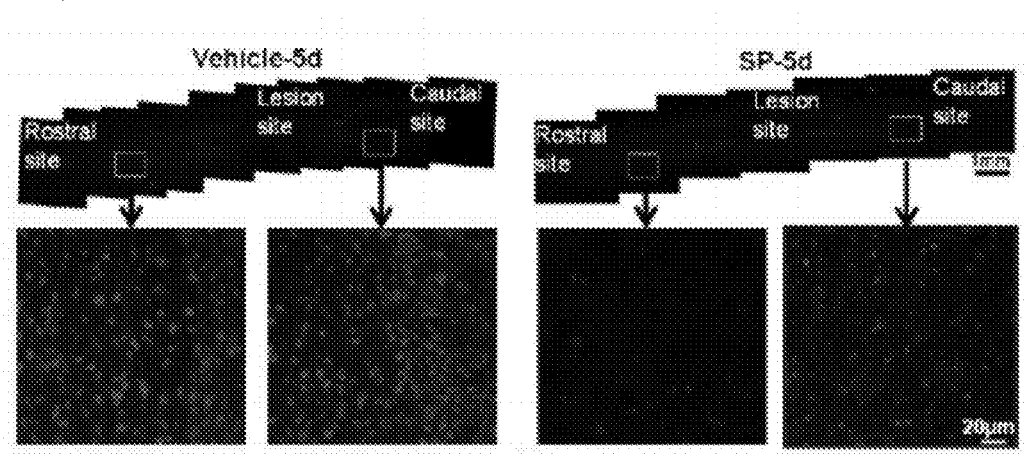
[Figure 1]

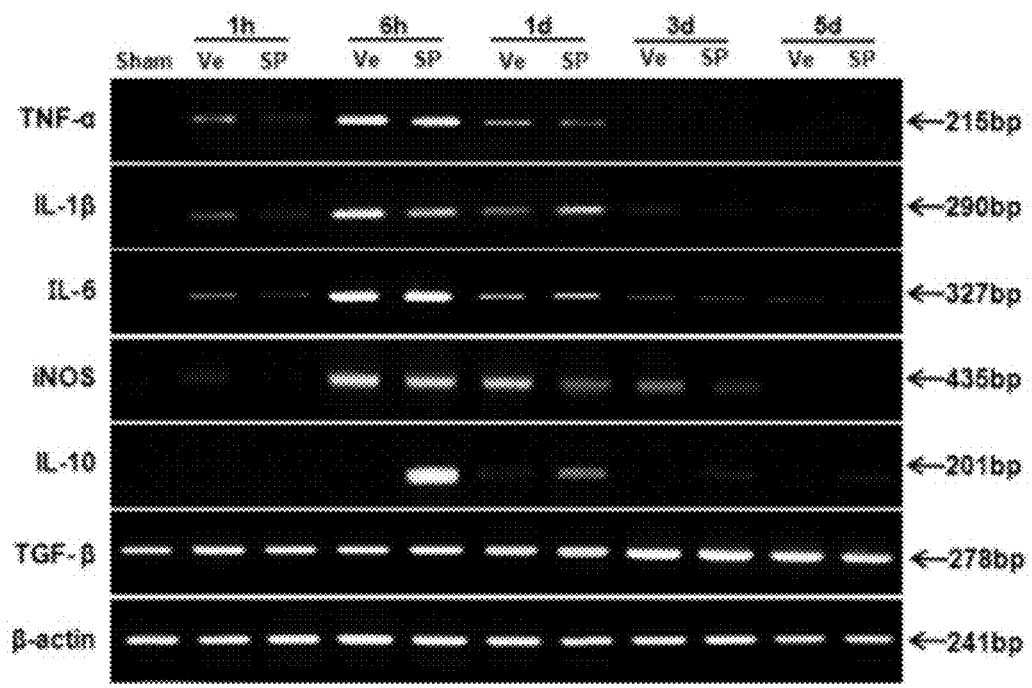
[Figure 2]

[Figure 3]
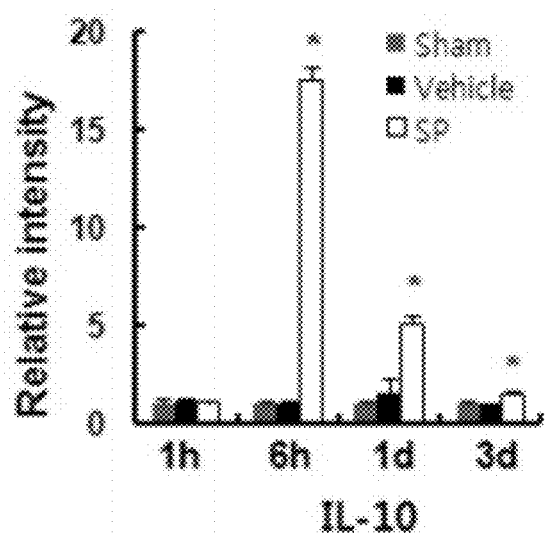
[Figure 4]
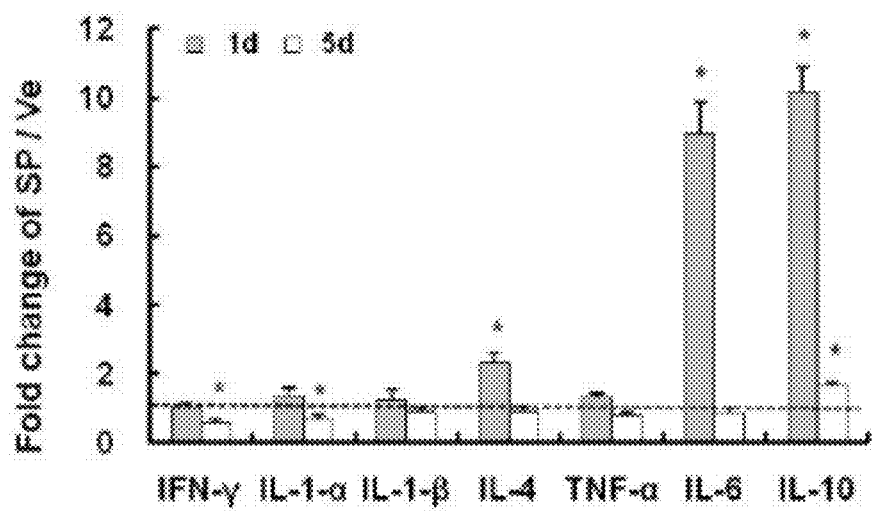

[Figure 5]
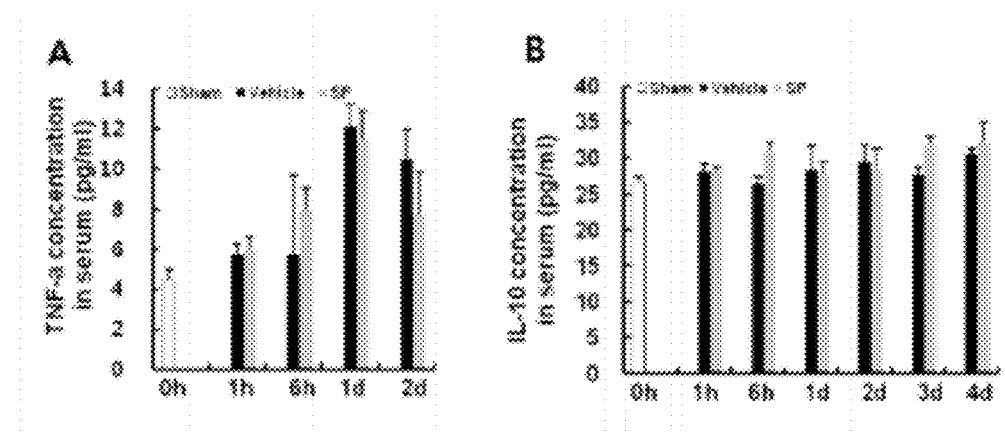

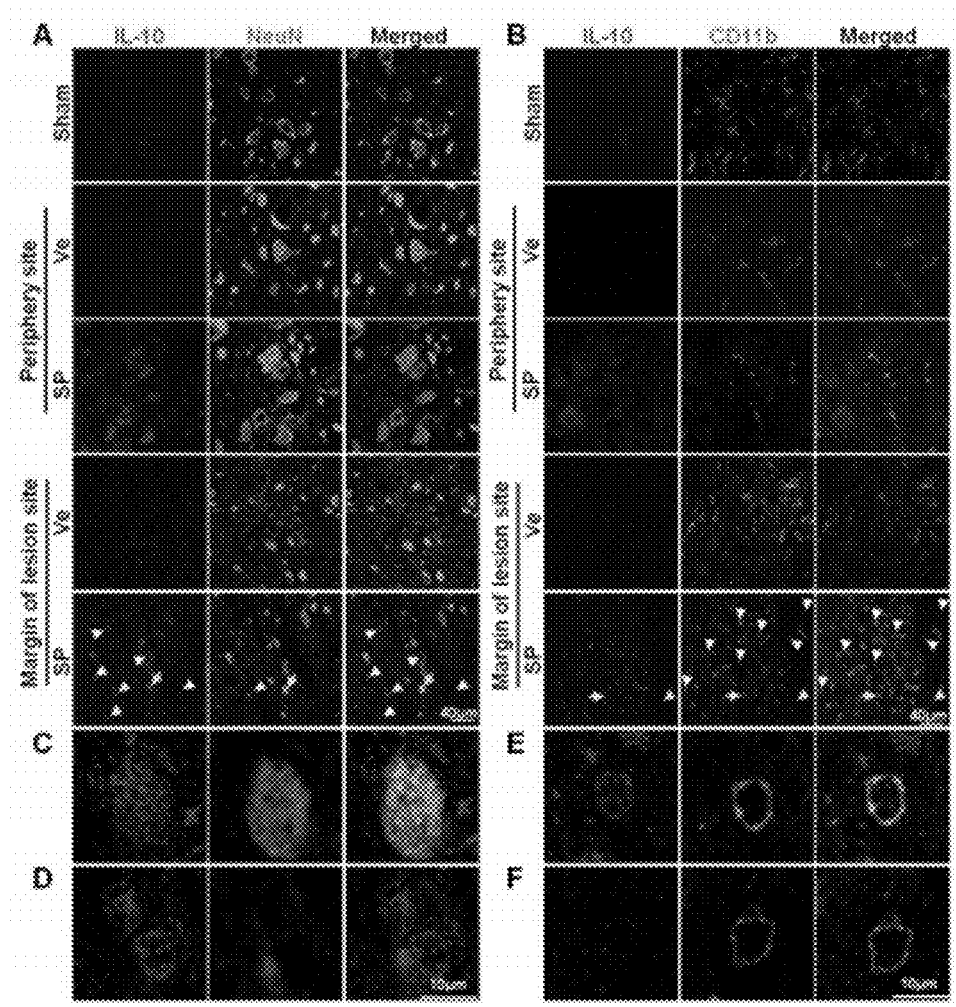

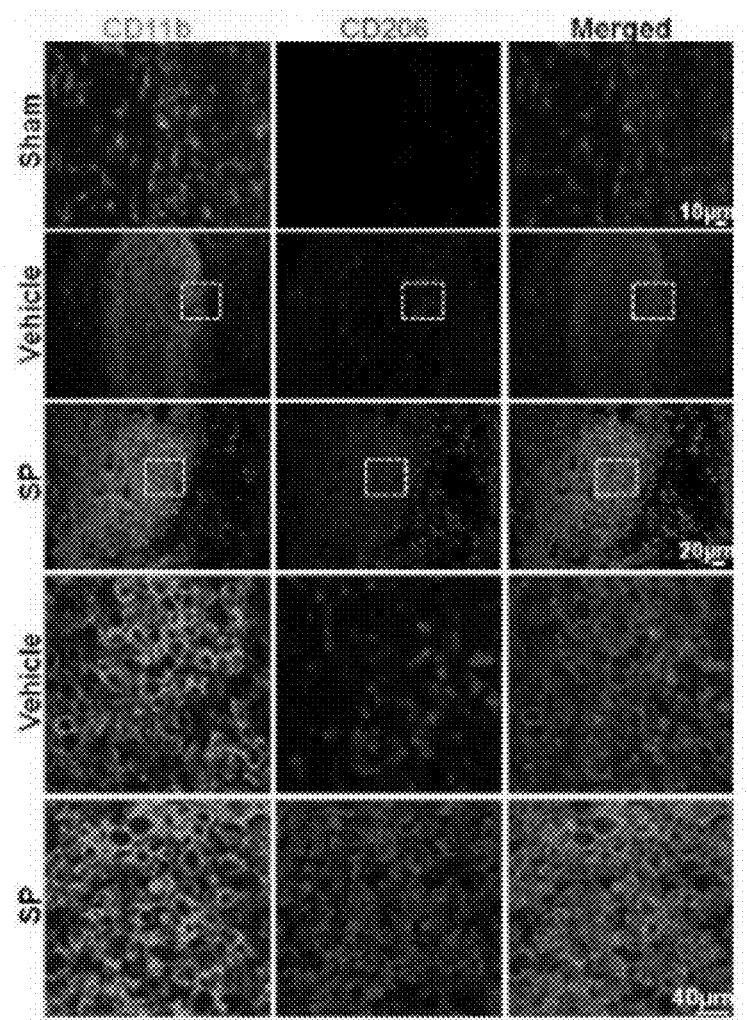
[Figure 7]

[Figure 8]
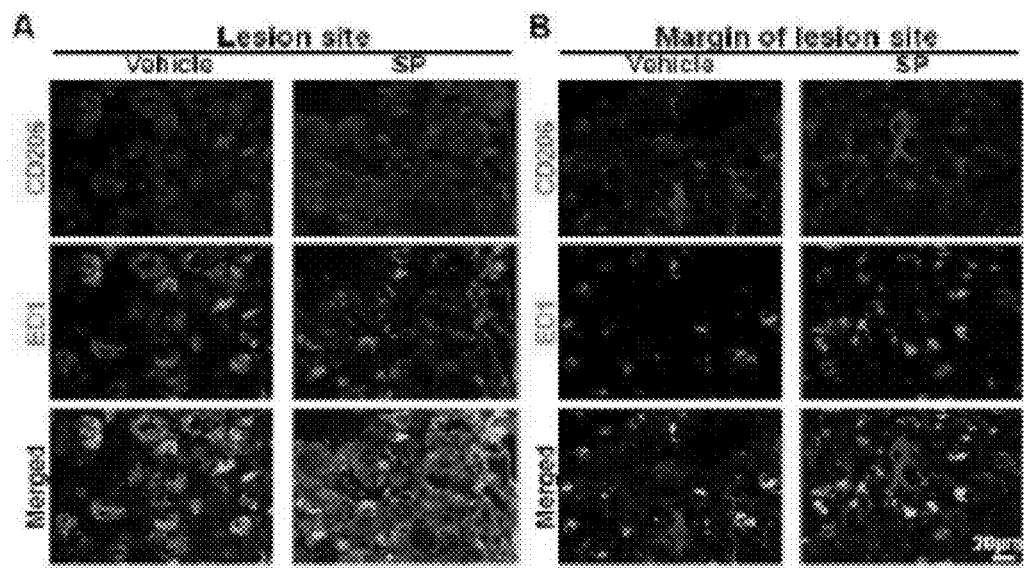
[Figure 9]
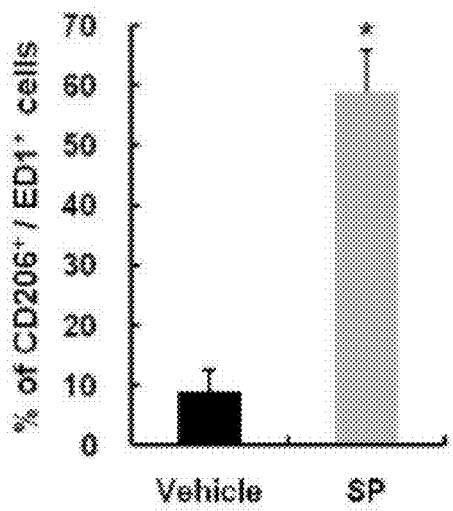

[Figure 10]
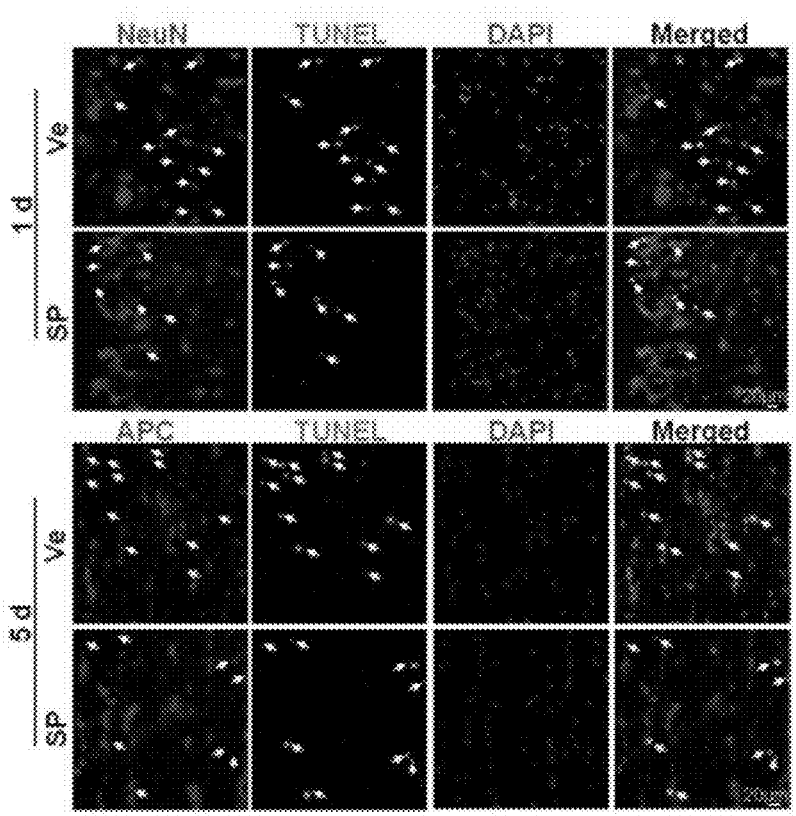
[Figure 11]
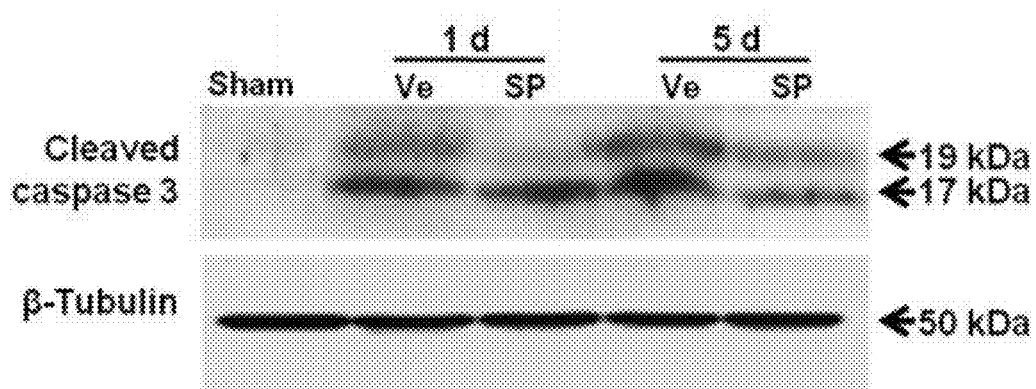

[Figure 12]
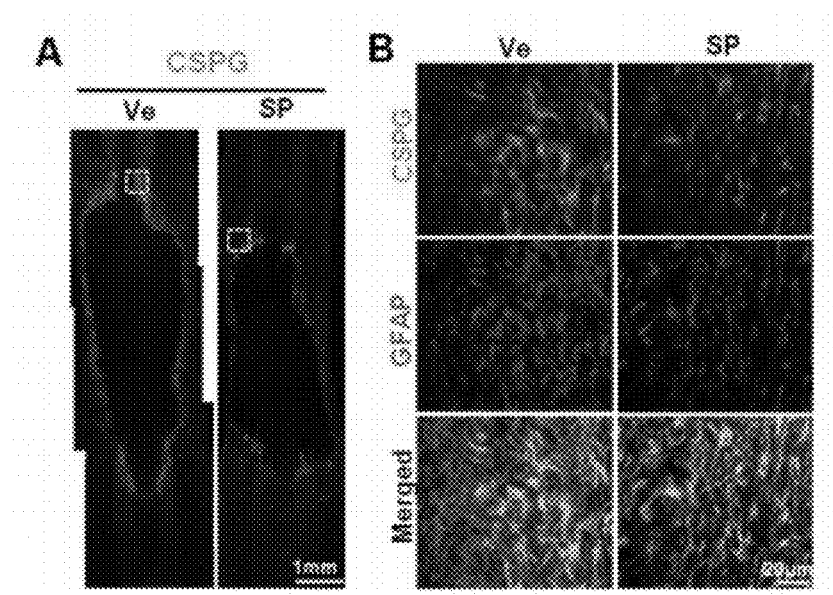
[Figure 13]
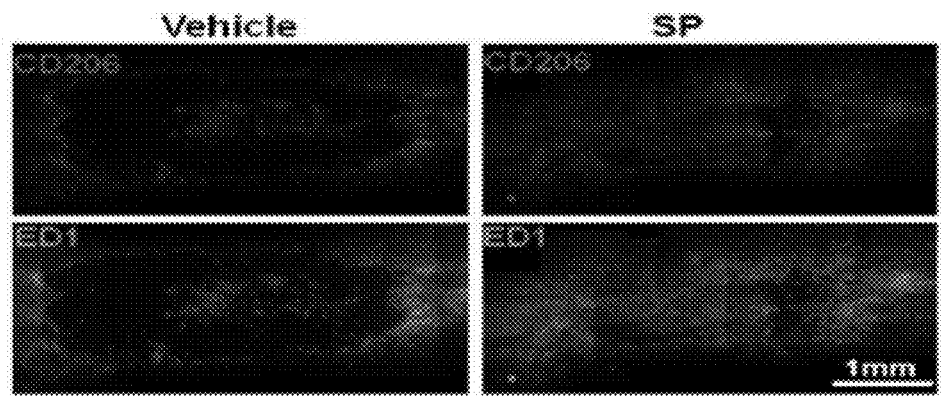

[Figure 14]
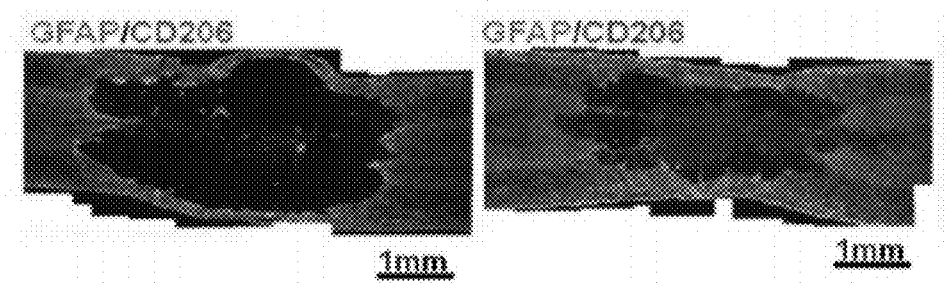
[Figure 15]
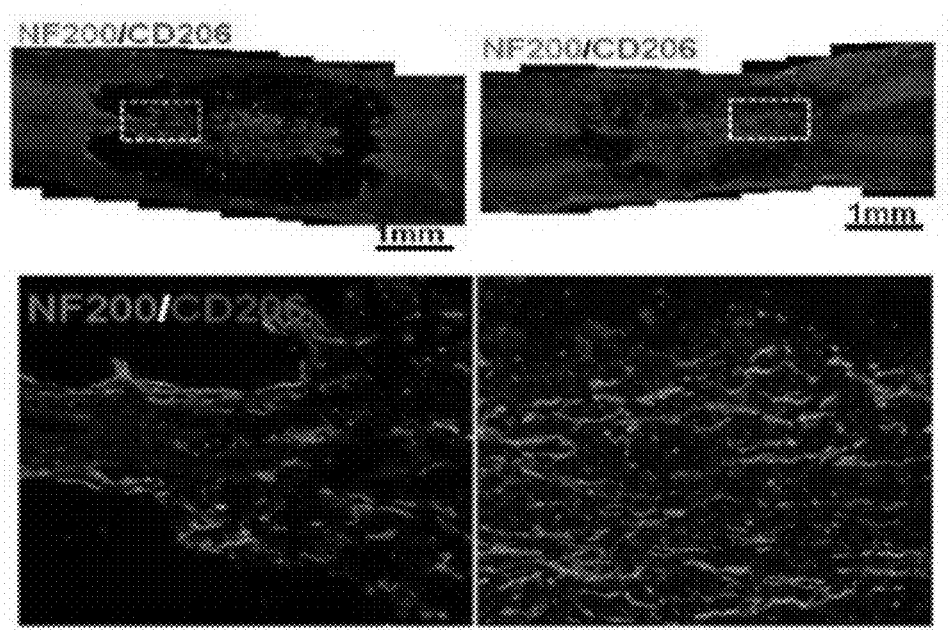

[Figure 16]
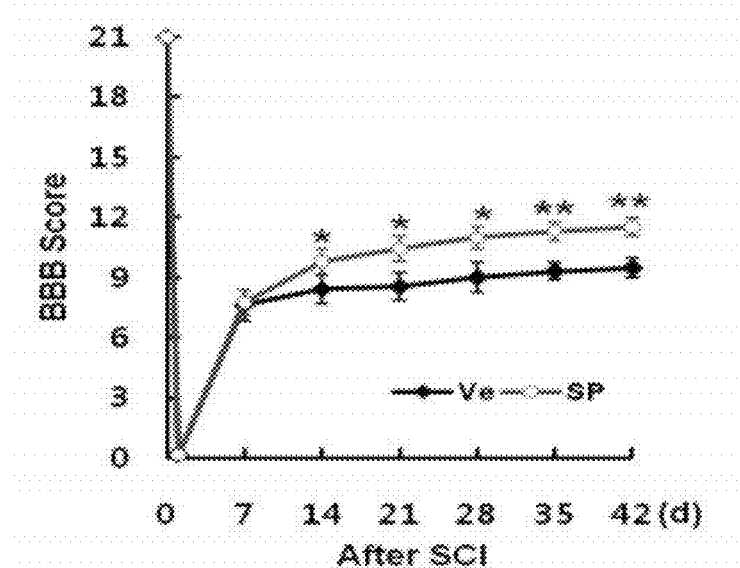
[Figure 17]
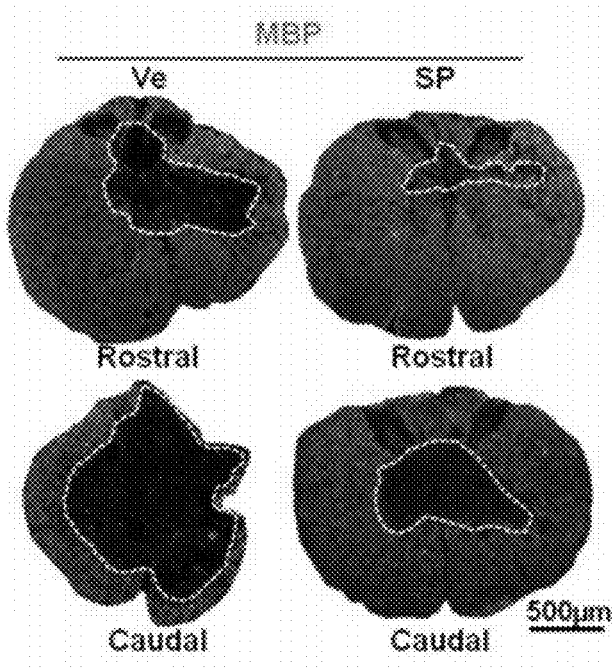

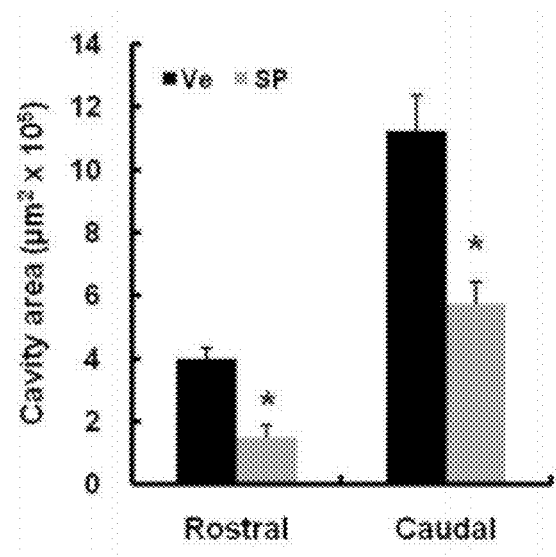
[Figure 18]

COMPOSITION FOR PREVENTING OR TREATING A SPINAL CORD INJURY

CROSS REFERENCE TO RELATED APPLICATIONS

This application is a U.S. national stage application filed under 35 U.S.C. §371 of International Patent Application PCT/KR2010/005419, accorded an international filing date of Aug. 17, 2010, which claims the benefit of Korean (KR) Application No. 10-2009-0075880 filed Aug. 17, 2009.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920124.401USPC_SEQUENCE_LISTING.txt. The text file is 2 KB, created on May 11, 2012, and is being submitted electronically via EFS-Web.

TECHNICAL FIELD

The present invention relates to a composition comprising Substance P for preventing or treating a spinal cord injury.

BACKGROUND ART

A patient suffering from a spinal cord injury is rapidly increasing due to the fact that the pace of economic development is accelerating. As a result, social medical expenses are increasing thereby causing serious economic losses. Most patients suffered from a spinal cord injury are young and involved in a lot of activities, so remarkable personal and national losses may be anticipated when taking their productivities of lifetimes into consideration. In addition, permanent losses of motor skill and sensory function due to a degeneration of nerve centre may degrade the quality of one's individual life, and may psychologically and economically affect on protectors who support patients, thereby causing severe social and cultural adverse reactions. Thus, a method of treating the spinal cord injury and a development of drug are sincerely required.

The spinal cord injury causes sudden paralysis thereby causing a functional impairment of various parts so that it has a risk factor that may cause a variety of complications. The neuropathy does not limit to a nerve knot that is directly pressed, but is generated over widely nerve that is presented below a nerve knot. In addition, physiological functions that are damaged after a traumatic injury are not stopped as they are, but deteriorated worse and worse (el Masry W S, Short D J., 1997).

A study published in 1997 found that when a spinal cord injury is generated, an excitotoxicity neurotransmitter, a free radical, inflammatory mediators, and the like are generated so that apoptosis is induced. Recently, after revealing that an unsuitable environment for nerve regeneration is made due to a formation of glial scar (Liu X U et al., 1997, Fitch M T, Silver J., 2008), a lot of researchers are focusing on developing a treatment method that can help a recovery of a nerve function and minimize a neuropathy. However, there is only a methylprednisolone treatment that acts to decrease a damage of a nervous tissue within 24 hours after damaging, that is, in an acute phase, in which the methylprednisolone treatment is recognized as a treatment of a spinal cord injury through a clinical test (Bracken et al., 1990). However, the curative power of the methylprednisolone treatment is insignificant and its utility is still highly controversial (Schwab et al., 1996). Therefore, scientists all over the world studied tissue and cell transplants, an injection of neurotrophin, a production of neurotrophin using gene therapy, a microsurgery, an injection of a combination, and the like by actively progressing a study about all types of agents for a neuro-protective therapy. That is, until now, there remain no effective treatments to improve neurological outcomes following SCI. Accordingly, a development of drug for recovering the spinal cord injury is more urgently needed.

The spinal cord injury is mainly caused by pressing a spinal cord through a displacement of spine due to a traumatic injury. A necrosis is caused immediately after damaging along with a mechanical primary damage, apoptosis of oligodendrocyte in the white matter and a neuronal cell of a grey matter is caused due to a slowly generated apoptosis, and a demyelination of axon is caused thereby ultimately generating a permanent functional disorder. Considering its pathophysiologic analysis, main causes of apoptosis are known as the following factors: an excitotoxicity due to a large amount of glutamate initially isolated in a damaged site after damage of spinal cord injury; an oxidative stress due to an active oxygen (ROS); ATP depletion; an ischemia due to an hypoxia environment, and then; an inflammation due to inflammatory mediators, such as iNOS, or proinflammatory cytokines, such as TNF-α, IL-1β, and the like; and the like (Lu et al., 2000, Kapoor et al., 2003). Among these factors, the inflammatory reaction lasts through a long period as well as at the very beginning. Especially, apoptosis that slowly progresses or an inflammatory reaction due to microglia in axon degeneration is pathologic property that is commonly exhibited in most nerve diseases as well as a spinal cord injury so that it is known that its regulation is important to prevent an expansion of disease of a nerve system (Beattie, 2004).

A senile dementia, which is known as the global disease giving pains to many people, is one of central nervous system diseases. There are various factors causing the senile dementia, and about 50% of the diseases is Alzheimer-type dementia, and 20~300 of the diseases is a vascular dementia, a alcoholic dementia, a dementia due to Parkinson's disease, and the like. In addition, Parkinson's disease that is a representative degenerative cerebropathia is often accompanied by Alzheimer's disease or an amyotrophic lateral sclerosis thereby suggesting a common pathologic mechanism of degenerative brain disease. Considering a pathologic mechanism of nervous system diseases that are commonly generated, there are an abnormal accumulation of the most degenerative nervous diseases, such as a senile dementia, Parkinson's disease, a bovine spongiform encephalopathy, Huntington's disease, an amyotrophic lateral sclerosis and the like, and protein condensation and deposition therefrom. The deposits induce an oxidative stress in a nerve cell and decrease a mitochondria function thereby inducing apoptosis, and also the destruction product generated for this reason acts as an immunity-inflammation stimulating factor thereby activating a complement pathway and a microglia, and an inflammatory reaction is accelerated by a positive feedback to stimulate a degeneration change (McGeer et al., 1995, Kohutnicka et al., 1998, Alexianu et al., 2001).

Meanwhile, it is known that all sorts of central nervous diseases are involved in apoptosis of nerve cell. For example, cells having a part reflecting a light and shade line as a progressive process of ischemic injury for a stroke will die for a period of weeks due to apoptosis (Lo et al., 2003). In addition, apoptosis breaks out at a dopamine nerve cell that is presented at a brain substantia nigraas due to reasons, such as an oxidative stress, a mitochondria dysfunction, a death receptor, and the like, for Parkinson's disease that is a degenerative central nervous system disease (Tansey et al., 2007). And also, apoptosis breaks out due to an amyloid beta protein for Alzheimer's disease (Tesco et al., 2003). Accordingly, it was revealed that apoptosis is the main cause of an amyotrophic lateral sclerosis that selectively loss of motor neuron, Huntington's disease that induces apoptosis by a fatal genetic disorder, and all sorts of mental diseases (Mattson et al., 2008). It can be expected from the above results that a development of drug that can prevent apoptosis is essential to treating Parkinson's disease, Alzheimer's disease, an amyotrophic lateral sclerosis, Hungtington's disease, which are degenerative central nervous system diseases, a depressive disorder, an epilepsy, and the like, which have similar mechanisms as a spinal cord injury and a stroke, as well as a spinal cord injury and a stroke, and also marketability thereof is enormous.

Meanwhile, the most important measurement of recovery from a spinal cord injury may be a result of observing the behavioral change thereof, and thus it may be based on BBB locomotor rating scale measuring a loss and recovery of motor skill shown after a spinal cord injury (Basso et al., 1995).

Substance P (hereinafter, also called as to 'SP') is a peptide consisting of 11 amino acids, and widely distributed at a nervous tissue (Kramer et al., 1998) and various organs (skin, salivary glands, lung, pancreas, kidney, bladder, prostate) (Kohlmann et al., 1997, Rupniak and Kramer., 1999). Especially, Substance P is generated at a dorsal root ganglion, and largely distributed at a posterior column of spinal cord, and Substance P is also found at a peripheral process and a central C fiber in a peripheral nervous system (Radhakrishnan and Henry., 1995, Henry., 1993, Vaught 1988). A noxious stimulus occurs by involving in a pain as a physiological function thereby secreting Substance P from primary afferent terminals affecting a neurokinin 1 receptor, and then activating $2^{nd}$ messenger to induce influx of calcium ions. It is known that an increase of calcium ion influx accelerates a generation of nitric oxide, and the resulting nitric oxide increases release of Substance P by a feedback thereby forming a hypersensitization through signaling pathways of Substance P (Radhakrishnan and Henry., 1995, Chatani et al., 1995). The mechanism involved in a pain largely limits possibility of developing a drug treating agent of Substance P in central nervous system injury and degenerative diseases by a researcher.

Besides this, it is reported and known that Substance P is involved in inducing various inflammatory reactions in a peripheral nervous system and also in treating an injury by increasing penetrability of endotheliocyte and vasodilation (Matthay M A and Ware L, 2004). Accordingly, the present inventors had identified that an administration of Substance P accelerates an injury treatment after injuring in a cornea injury model.

Since then, the present inventors found that Substance P is involved in killing a central nervous cell that is generated after a spinal cord injury, and contributes greatly to a recovery of motor skill so that we could complete the present invention through repeated researches.

DISCLOSURE

Technical Problem

The present inventors attempt to provide a composition for treating a spinal cord injury, a composition for inhibiting apoptosis, a composition for decreasing microglia activity, an anti-inflammatory composition, and the like, in which the compositions include Substance P as an active ingredient.

Technical Solution

The present invention provides a composition for treating or preventing a spinal cord injury, in which the composition includes Substance P as an active ingredient.

Also, the present invention provides a composition for treating or preventing a traumatic spinal cord injury or a non-traumatic spinal cord injury, in which the composition includes Substance P as an active ingredient.

The traumatic injury may be a flexion injury, a vertical compression injury, a hyperextension injury, a flexion-rotation injury, and the like, but is not limited thereto. The traumatic spinal cord injury may be caused by traffic accidents, a fall, a sport injury, an attack, and the like. The non-traumatic injury may be a vascular dysfunction, an arthritis, a degenerative arthritis, a vertebral subluxation, a myelitis, a transverse myelopathy, a syringomyelia, a spinal cord tuberculosis, and the like, but is not limited thereto.

Also, the present invention provides a composition for inhibiting apoptosis, in which the composition includes Substance P as an active ingredient.

Also, the present invention provides a composition for treating a spinal cord injury caused by apoptosis, or a composition for preventing or treating a degenerative central nervous system disease caused by apoptosis.

In addition, the present invention provides a composition for preventing or treating a degenerative central nervous system disease, in which the composition includes Substance P as an active ingredient.

For the present invention, the degenerative central nervous system disease may be a stroke, Parkinson's disease, Alzheimer's disease, an amyotrophic lateral sclerosis, Huntington's disease, a depressive disorder, an epilepsy, and the like.

Also, the present invention provides a composition for decreasing a microglia activity, in which the composition includes Substance P as an active ingredient.

The composition comprising Substance P as an active ingredient according to the present invention may be prepared by using pharmaceutically-suitable and physiologically-acceptable additives in addition to the active ingredient, and the additives may be excipients, a disintegrant, a sweetener, a binder, a coating agent, an inflating agent, a glidant, a lubricant, a flavoring agent, and the like.

The composition comprising Substance P as an active ingredient according to the present invention may be formulated as a pharmaceutical composition by additionally including at least one of pharmaceutically acceptable carriers in addition to the above-mentioned active ingredient in order to administrate.

A pharmaceutical formulation of the composition comprising Substance P as an active ingredient may be granules, powders, tablets, coated tablets, capsules, syrup, juice, a suspension, an emulsion, an ointment, cream, gel, medicinal drops, aerosol, an injectable liquid formulation, and the like.

For example, an active ingredient may be combined with an oral and non-toxic pharmaceutical acceptable inert carrier, such as ethanol, glycerol, water, and the like, in order to formulate as a type of tablets or capsules. In addition, if it is necessary or required, suitable binding agent, lubricants, disintegents and coloring agents may be also included as a mixture. The suitable binding agent includes starch, gelatin, natural sugars, such as glucose, or beta-lactose, corn sweetening agents, natural or synthetic gums, such as acacia, tragacanth, or sodium oleate, sodium stearate, magnesium stearate, sodium benzoate, sodium acetate, sodium chloride, and the like, but is not limited thereto. The disintegrant includes starch, methylcellulose, agar, bentonite, xanthan gum, and the like, but is not limited thereto.

A pharmaceutically acceptable carrier for a composition formulated as a liquid solution may be suitable for a sterilization and a body, and may be saline solution, sterilized water, Ringer solution, butter saline solution, albumin injection solution, dextrose solution, malto dextrin solution, glycerol, ethanol, and the mixture of at least one thereof, and other general additives, such as antioxidants, a buffering solution, bacteristat, and the like may be added as needed. In addition, tablets, granules, capsules, a pill, a dosage form for injecting, such as an aqueous solution, suspension, an emulsion, and the like may be formulated by additionally adding a diluent, a dispersing agent, a surfactant, a binding agent, and a lubricant. Furthermore, it may be preferably formulated according to each use or each component by using the method as disclosed in Remington's Pharmaceutical Science, Mack Publishing Company, Easton Pa. as a suitable method in the related art.

The present invention provides a use of a composition comprising Substance P as an active ingredient for preventing or treating a spinal cord injury.

In addition, the present invention provides a use of a composition comprising Substance P as an active ingredient, for preventing or treating a traumatic spinal cord injury or a non-traumatic spinal cord injury. The traumatic injury may be a flexion injury, a vertical compression injury, a hyperextension injury, a flexion-rotation injury, and the like, and the non-traumatic injury may be a vascular dysfunction, an arthritis, a degenerative arthritis, a vertebral subluxation, a myelitis, a transverse myelopathy, a syringomyelia, a spinal cord tuberculosis, and the like, but they are not limited thereto. The traumatic spinal cord injury may be caused by traffic accidents, a fall, a sport injury, an attack, and the like.

Also, the present invention provides a use of a composition comprising Substance P as an active ingredient for inhibiting apoptosis, and also a use for treating a spinal cord injury caused by apoptosis, or a use for treating a degenerative central nervous system disease caused by apoptosis.

Furthermore, the present invention provides a use of a composition comprising Substance P as an active ingredient for preventing or treating a degenerative central nervous system disease. For the present invention, the degenerative central nervous system disease may be a stroke, Parkinson's disease, Alzheimer's disease, a amyotrophic lateral sclerosis, Huntington's disease, a depressive disorder, an epilepsy, and the like.

Also, the present invention provides a use of a composition comprising Substance P as an active ingredient for decreasing a microglia activity.

The present invention provides a method of preventing or treating a traumatic spinal cord injury or a non-traumatic spinal cord injury, in which the method includes administrating a therapeutically effective amount of Substance P to a mammal. For the present invention, the traumatic injury may be a flexion injury, a vertical compression injury, a hyperextension injury, a flexion-rotation injury, and the like, and the non-traumatic injury may be a vascular dysfunction, an arthritis, a degenerative arthritis, a vertebral subluxation, a myelitis, a transverse myelopathy, a syringomyelia, a spinal cord tuberculosis, and the like.

For the present invention, the traumatic spinal cord injury may be caused by traffic accidents, a fall, a sport injury, an attack, and the like.

Also, the present invention provides a method of preventing or treating a spinal cord injury caused by apoptosis or a method of preventing or treating a degenerative central nervous system disease caused by apoptosis, administering a therapeutically effective amount of Substance P as an active ingredient to a mammal.

Also, the present invention provides a method of preventing or treating a degenerative central nervous disease, in which the method includes administrating a therapeutically effective amount of Substance P to a mammal.

For the present invention, the degenerative central nervous system disease may be a stroke, Parkinson's disease, Alzheimer's disease, an amyotrophic lateral sclerosis, Huntington's disease, a depressive disorder, epilepsy, and the like.

As used herein, the term "a therapeutically effective amount" refers to the amount of active ingredient or pharmaceutical composition that induces a biological or medical reaction in an animal or a human that may be considered by researchers, vets, doctors, or other clinicians, and includes the amount of inducing alleviation of symptoms of disease or disorder to be treated. It is clear by a person who has a common knowledge in the related art that an effective administration amount and administration number for treating to an active ingredient of the present invention vary according to a required effect. Accordingly, an optimal dose to be administrated is easily determined by a person who has a common knowledge in the related art, and can be controlled by various factors, such as a type of disease, severity of disease, the amounts of an active ingredient and other components included in a composition, a type of dosage form, and an age, a weight, a general health condition, a sex, and a diet of a patient, an administration time, an administration route, a secretion rate of composition, a treating period, a drug of simultaneous use, and the like. For a method of treating a degenerative central nervous system disease, for example a stroke, Parkinson's disease, Alzheimer's disease, a amyotrophic lateral sclerosis, Huntington's disease, a depressive disorder, an epilepsy, and the like, according to the present invention, it is preferable that a volume of 0.001~0.5 mg/day, preferably 0.0001~0.005 mg/kg of Substance P is administrated in case of an adult when administrating one time per a day.

The composition according to the present invention may be administrated to an oral, subglossal, rectal, dermal, subcutaneous, intra-muscular, intra-abdominal, intra-venous, intra-arterial, intrathecal, intra-medullar route, and the like, and preferably may be administrated to a vein.

Advantageous Effects

Substance P according to the present invention exhibits effects of treating spinal cord injury, decreasing microglia activity, decreasing proinflammatory cytokines, inhibiting apoptosis, recovering/improving a motor skill, and the like. This indicates new functions of Substance P that are different from the conventional research results involved in a pain or inflammation in a nerve system. Especially Substance P is expected as an important candidate material for discovering new treating drug for a central nervous system disease, such as a spinal cord injury, a dementia, a stroke, and the like.

DESCRIPTION OF DRAWINGS

FIG. 1 is a diagram confirming a decrease of microglia/macrophage activity by Substance P at a spinal cord injury site;

FIG. 2 is a diagram showing a profile of expression of cytokine involved in inflammation by Substance P at a spinal cord injury site;

FIG. 3 is a graph showing a profile of expression of Interlukin-10 (IL-10) by Substance P at a spinal cord injury site;

FIG. 4 is a graph showing a result of antibody array analysis on cytokine changes by Substance P at a spinal cord injury site;

FIG. 5 is a diagram confirming effects on cytokines in a peripheral blood when administrating Substance P in a spinal cord injury model (FIG. 5A: TNF-α, FIG. 5B: IL-10);

FIG. 6 is a diagram confirming an increase of IL-10 expression in a nerve cell and oligodendrocyte by Substance P after a spinal cord injury;

FIG. 7 is a diagram comparing phenotypes of microglia/macrophage at a spinal cord injury site;

FIG. 8 is a diagram comparing phenotypes of microglia/macrophage at a spinal cord injury site and around a spinal cord injury site;

FIG. 9 is a graph showing profiles of ED1+ cell and CD206+/ED1+ cell by administrating Substance P in a spinal cord injury model;

FIG. 10 is a diagram confirming a decrease of apoptosis by Substance P at a spinal cord injury site through TUNEL staining;

FIG. 11 is a diagram confirming a decrease of apoptosis by Substance P at a spinal cord injury site through Western blotting;

FIG. 12 is a diagram confirming a decrease of CSPG by Substance P in a spinal cord injury model;

FIG. 13 is a diagram confirming an increase of CD206+/ED1+ double positive cells distribution by Substance P in a spinal cord injury model;

FIG. 14 is a diagram confirming an increase of GFAP-positive cells distribution by Substance P in a spinal cord injury model;

FIG. 15 is a diagram confirming a preservation of nerve fiber micro protein by Substance P in a spinal cord injury model;

FIG. 16 is a diagram showing a result of observing a behavioral change by a spinal cord injury;

FIG. 17 is a diagram confirming an effect of Substance P in protecting myelin sheath of a nerve cell in a spinal cord injury model; and FIG. 18 is a graph showing an effect of Substance P in protecting myelin sheath of a nerve cell in a spinal cord injury model.

MODE FOR INVENTION

Advantages and features of the present invention, and a method for achieving them will be clarified with reference to examples that will be described later. The present invention may, however, be embodied in different forms and should not be construed as limited to the examples set forth herein. Rather, these examples are provided so that the disclosure of the present invention will be thorough and complete, and will fully convey the scope of the present invention to those skilled in the art. The scope of the present invention should be defined by the appended claims.

EXAMPLE

Example 1

Confirmation of Effect of Decreasing Microglia/Macrophage Activity by Substance P (1) Establishment of Spinal Cord Injury Model and Administration of Substance P For the present experiment, male white mice (Sprague-Dawley 240-250 g, 7 weeks, 10 mice) were under general anesthetics by an intraperitoneal injection of Ketamin (80 mg/kg, Yuhan Corporation) and Rompun (7.4 mg/kg, Bayer Korea Corporation). Laminectomy was performed at spine T9-10 level to expose a spinal cord keeping intact dura. And then, rat was put on Spinal cord dropping device (NYU); spine processes at T8 and T11 sites were fixed by using a clamp, respectively; then, a rod (diameter 2 mm, weight 10 g) was dropped from 25 mm height vertical to dorsal part of spinal cord followed by suturing injury site muscle and skin. The rat of Sham-operated control group was performed only laminectomy at same area without damaging spinal cord injury (marked by 'sham" in figures; hereinafter, the same as above).

Substance P (marked by 'SP' in figures; hereinafter, the same as above) dissolved in saline of 5 nmol/kg concentration was injected through tail vein at immediately, 24 hours, and 48 hours after a spinal cord injury for experimental groups. At sham control group, same volume of saline (marked by 'vehicle' in figures; hereinafter, the same as above) without Substance P was injected at same time points. Operation were performed on an electric heating pad of 37° C., and then rat were transferred to cage after awake from the anesthetic.

(2) Preparation of Tissue

For anesthetization, Ketamin (80 mg/kg) and Rompun (7.4 mg/kg) were intra-abdominally injected at 5 days after operation. Then, perfusion was performed by opening the of heart and pumping 200 ml of a physiological saline and 4% paraformaldehyde (Sigma) through right atrium of heart. Then, a segment of spinal cord with injury site was removed and put in 4% paraformaldehyde at 4° C. for 6 hours. Subsequently, spinal cords were washed with saline, and placed in 30% sucrose (Sigma) solution at 4° C. overnight. Next day, spinal cords were cut in a length of 1.5 cm in which the injured site is localized in epicenter followed by embedding in OCT compound (optimal cutting temperature compound, Sakura). The fixed tissues were cut in a thickness of 10 μm (Longitudinal section) or 20 μm (cross section) with Cryostat (Leica) and attached to slide. Finally, slides were stored at −80° C.

(3) Immunofluorescence Staining

The selected sections for immunofluorescence staining were washed with saline for three times, and blocked with 10% horse serum (Jackson ImmunoResearch) for 1 hour at a room temperature. ED1 antibody (1:200, Milipore), a marker for activated microglia/macrophage, was treated and placed at 4° C. overnight. Next day, slides were washed with saline, and treated with a secondary antibody conjugated with Alexa Fluor 488 (1:400, Invitrogen) or cyanine 3 (1:500, Jackson ImmunoResearch) for 1 hour at room temperature. Then, washing twice with saline, slides were mounted with Vestashield mounting medium (DAPI, Vector Laboratories, Burlingame, Calif.) including DAPI (4,6-diamidino-2-phenylindole). Finally, slides were observed with Leica CTR 4000 Fluorescence microscopy or Zeiss LSM 510 META confocal microscopy, and the results were shown in FIG. 1.

FIG. 1 shows a distribution of activated microglia/macrophage expressing ED1 antigen in experimental group and control group. The activated microglia/macrophage expressing ED1 antigen was significantly decreased in experimental group compared with the control from rostal to caudal area. Although it was not shown in Figures, in the sham-operated group, activated microglia/macrophage was not observed. Accordingly, it indicated that Substance P decreases microglia/macrophage activity, which means that through this function Substance P plays an important role in recovering after spinal cord injury.

Example 2

Confirmation of Effect of Decreasing Inflammation by Substance P after Spinal Cord Injury (1) Extraction of Total RNA from Spinal Cord and RT-PCR Analysis of Cytokine Substance P (5 nmol/kg in saline) or saline (the same volume without Substance P) was injected through tail vein at various time points at immediately, 1 d, 2d after operation as (1) of Example 1. At 1 hour, 6 hours, 1 day, 3 days, and 5 days, the experimental group (6 rats/group) and the control (6 rats/group) were sacrificed, respectively. After exposing a spinal cord by laminectomy, spin cord with a length of 1 cm, the injury site between T9-10 as the central, was quickly cut off, and immediately put into liquid nitrogen. Total RNA was extracted by using Trizol reagent (Invitrogen), and the cDNA was synthesized through Reverse transcription process. Then, PCR (Chromagen) was performed using primers of TNF-α IL-1β iNOS. The results were shown in FIG. 2. Primer's sequences and PCR conditions were as follows.

expression of inflammatory cytokine and induces the expression of anti-inflammatory cytokine.

(2) Rat Cytokine Antibody Array Analysis

A rat cytokine antibody array analysis was performed in order to investigate an effect of Substance P in expressing cytokine.

At immediately, 1 d, and 2d, Substance P or saline (the same volume without Substance P) was injected through tail vein using the same method as (1) of Example 1. After operating, the experimental group (4 rats/group) and the control (4 rats/group) were sacrificed at 1 d and 5d, respectively. The spinal cord tissue (1 cm) obtained from an animal was homogenized with a dissolution buffer solution (10% glycerol, 20 mM Tris [pH 8.0], 137 mM NaCl, 1% Nonidet P-40, 0.5 mM EDTA, 10 mM $Na_2P_2O_7$, 10 mM NaF, 1 μg/ml aprotinin, 10 μg/ml leupeptin, 1 mM vanadate and 1 mM PMSF). A protein amount of supernatant was determined by BCA assay (Pierce). Subsequently, a cytokine assay was performed according to instructions of Ray Biotech Morcross GA protocol. A membrane was blocked with a blocking buffer solution, then 150 μg of a protein sample was added,

|         | Primer Sequence | PCR Parameter (Tem. Hour) | Cycle No. | Product Size (bp) |
|---------|-----------------|----------------------------|-----------|-------------------|
| TNF-α   | 5'-CCCAGACCCTCACACTCAGAT-3' (sense) (SEQ ID NO: 1) 5'-TTGTCCCTTGAAGAGAACCTG-3' (antisense)(SEQ ID NO: 2) | 94° C.-30s 55° C.-30s 72° C.-30s | 30 | 215 |
| IL-1β   | 5'-GCAGCTACCTATGTCTTGCCCGTG-3' (sense) (SEQ ID NO: 3) 5'-GTCGTTGCTTGTCTCTCCTTGTA-3' (antisense) (SEQ ID NO: 4) | 94° C.-30s 50° C.-30s 72° C.-30s | 30 | 290 |
| IL-6    | 5'-AAGTTTCTCTCCGCAAGATACTTCCAGCCA-3' (sense) (SEQ ID NO: 5) 5'-AGGCAAATTTCCTGGTTATATCCAGTTT-3' (antisense) (SEQ ID NO: 6) | 94° C.-30s 55° C.-30s 72° C.-30s | 30 | 327 |
| iNOS    | 5'-CTCCATGACTCTCAGCACAGAG-3' (sense) (SEQ ID NO: 7) 5'-GCACCGAAGATATCCTCATGAT-3' (antisense) (SEQ ID NO: 8) | 94° C.-30s 55° C.-30s 72° C.-30s | 30 | 435 |
| IL-10   | 5'-GAGTGTTCAAAGGGAAATTATAT-3' (sense) (SEQ ID NO: 9) 5'-CTGGTTTCTCTTCCCAAGAC-3' (antisense) (SEQ ID NO: 10) | 94° C.-30s 55° C.-30s 72° C.-30s | 30 | 201 |
| TGF-β   | 5'-GAGAGCCCTGGATACCAACTACTG-3' (sense) (SEQ ID NO: 11) 5'-CTCCACCTTGGGCTTGCGACCCAC-3' (antisense) (SEQ ID NO: 12) | 94° C.-30s 60° C.-30s 72° C.-30s | 30 | 278 |
| β-actin | 5'-CTTCTGCATCCTGTCAGCGATGC-3' (sense) (SEQ ID NO: 13) 5'-AGAAGAGCTATGAGCTGCCTGACG-3' (antisense) (SEQ ID NO: 14) | 94° C.-30S 58° C.-30s 72° C.-30s | 25 | 241 |

As shown in FIG. 2, the expressions of TNF-α, IL-1β, IL-6, and iNOS mRNAs for the experimental group at 1 hour after a spinal cord injury were slightly decreased as compared with the control. The expressions of the above-mentioned inflammatory cytokines at other times do not have a difference between two groups, but the expression of iNOS was surely decreased at one day after a spinal cord injury. In addition, as shown in FIG. 3, the expression of IL-10 mRNA, anti-inflammatory cytokine, was increased by at least 17 times at 6 hours and persist increasing level up to 3 day in Substance P-injected group as compared with the control after a spinal cord injury. This result suggests that Substance P inhibits the and reacted for 2 hours at a room temperature. The membrane was washed and 1 ml of primary antibody conjugated with a biotin was added, and placed at 4° C. overnight. Next day, the membrane was washed, and reacted with 2 ml of streptoavidin conjugated with horseradish peroxidase for 30 minutes at a room temperature. The membrane was developed using enhanced chemiluminescence-type solution, and the film was exposed to Radiography. Using USA NIH Image and Image J software (Hong et al., 2009), density quantification of array was performed. The results were shown in FIG. 4.

As shown in FIG. 4, the amounts of IL-4 and IL-10 at one day after a spinal cord injury were increased by two times and ten times, respectively by injecting Substance P. In addition, the amount of IL-10 was higher than the control at 5 d after spinal cord injury. The amount of IL-6, an inflammatory cytokine, was meaningfully increased at one day after a spinal cord injury. This result supports an increase of IL-10 expression and corresponds with the previous report, in which at T cell IL-27 and IL-6 induce IL-24 generation (Stumhofer et al., 2007). Additionally, the expressions of IFN-γ and IL-1α were slightly decreased in substance P-injected group at five days after a spinal cord injury as compared with the control.

(3) Whether Cytokine is changed in Peripheral Blood?—ELISA Assay

At immediately, 1 d, 2 ds, in order to investigate an effect of Substance P in cytokine in a peripheral blood, Substance P (5 nmol/kg in saline) or saline (the same volume without Substance P) was injected through tail vein, respectively using the same method as (1) of Example 1. After operating, serum was collected from the experimental group (4 rats/group) and the control (4 rats/group) at 1 hour, 6 hours, 1 day, 3 days, and 5 days, respectively. Finally, The levels of TNF-α and IL-10 were measured by using ELISA kit (R&D Systems). The results were shown in FIG. 5.

As shown in FIGS. 5A and 5B, the levels of TNF-α and IL-10 in peripheral blood were no meaningful differences between Substance P-injected group and the control.

Example 3

Confirmation of Increase of IL-10 Expression in Nerve Cell and Oligodendrocyte by Substance P after Spinal Cord Injury In order to confirm increasing IL-10 expression in cell when administrating Substance P after a spinal cord injury, immuno-histochemical staining was performed Using the same method as (1) of Example 1, Substance P or saline (the same volume without Substance P) was injected to a tail vein individually at immediately, 1 d, 2d after a spinal cord injury. After operating, the experimental group (4 rats/group) and the control (4 rats/group) were sacrificed. A tissue section was prepared by using the method as disclosed in (2) and (3) of Example 1, and in order for an immunofluorecence staining, the selected section was washed three times with saline, and blocked with 10% horse or rabbit serum (Jackson ImmunoResearch) for 1 hour at room temperature. Then, primary antibodies were added as follows: a marker to a nerve cell-specific antibody NeuN (1:100, Millipore); microglia/macrophage antibody CD11b (1:200, Milipore) and IL-10 (1:100 MBL, Nagoya, Japan). The slides were placed at 4° C. overnight. The next day, it was washed with saline, and then treated with a secondary antibody conjugated with Alexa Fluor 488 (1:400, Invitrogen) or cyanine 3 (1:500, Jackson ImmunoResearch) for 1 hour at a room temperature. After washing twice with saline, slides were mounted with Vestashield mounting medium (DAPI, Vector Laboratories, Burlingame, Calif.) including DAPI (4,6-diamidino-2-phenylindole). Finally, it was observed with Leica CTR 4000 Fluorescence microscopy or Zeiss LSM 510 META confocal microscopy, and the results were shown in FIG. 6.

IL-10 was scarcely expressed in normal rat as shown in FIG. 6. IL-10 was specifically expressed at a nerve cell from Substance P-injected rat at one day after a spinal cord injury. But in peripheral area of injured site, IL-10 was expressed in even other cells and not limited to nerve cell. As a result of confirmation, it was found out that around the injury site partially microglias or macrophages as well as nerve cells are expressing IL-10. These results first found out that what cells expressing IL-10 after Substance P-injection. Also it was re-found that an evidence as anti-inflammatory reaction IL-10 level was increased, which agree with results of FIGS. 2 to 4.

Example 4

Confirmation of Effect of Inducing of M2 Phenotype Macrophage by Substance P—MACS Assay Microglia and macrophage have an inflammatory macrophage phenotype (M1) and selectively activated macrophage phenotype (M2). M1 macrophage expresses TNF-α and iNOS and has a proteolysis activity, and M2 macrophage has an immunity control, a tissue recovery, and a tissue remodeling properties. MACS (Miltenyi Biotec, Bergisch Gladbach) assay was performed in order to determine a quantitative amount of M1 (ED1 positive, CD206 negative) and M2 (ED1 positive, CD206 positive) phenotype macrophages after Substance P-injection in a spinal cord injury model.

At immediately, 1 d, 2d, Substance P or saline (the same volume without Substance P) was injected to a tail vein after a spinal cord injury, using the same method as (1) of Example 1. After operating, the experimental group (4 rats/group) and the control (4 rats/group) were sacrificed at five days. A spinal cord with a length of 3 cm including the injury site was cut, and immediately put into an ice-cooling Ca—Mg-absent HBSS (Hank's balanced salt solution) buffer solution added with 1% penicillin-streptomycin (Gibco). Dura was removed by using a dissecting microscope, and cut in a length of 1 cm with the injury site as the central. A method modified from Yoo and Wrathall (Yoo and Walthall, 2007) was applied for the present invention. In short, each section was grinded, respectively, and digested in the solution of 50 U/ml DNase I (Sigma) and 0.25% Trypsin (Sigma) in HBSS solution at 37° C. for 10 minutes. Serum was added to inactivate trypsin, and centrifuged at 200 g for 10 minutes. A cell pellet was washed with HBSS, passed through a filter (BD Biosciences, Mississauga, Ontario) with a size of 70 μm pore, and washed with MACS buffer solution (Miltenyi Biotec) including 0.5% BSA. The sample was re-suspended in 0.5 ml of the same buffer solution, treated with a mouse anti-ED1 (1:100, Millipore) monoclonal antibody for 15 minutes in an ice, then washed with PBS, and centrifuged. The cell suspension suspended with 50 μl of buffer solution was treated with 20 μl of a rat anti-mouse MicroBeads (Miltenyi Biotech) for 10 minutes on an ice, and then washed with PBS. Magnetically labeled cells were collected by washing the column and then counted. Subsequently, in order to select CD206 positive cells from ED1 positive cells, the total elution liquid was washed twice with a buffer solution, and then passed through a new MACS column to confirm a complete removement of anti-mouse MicroBeads conjugated with ED1. There were no cells bonded to MACS column. A second MACS was performed with a rabbit anti-CD206 polyclonal antibody (1:100; Millipore) to the isolated cells. The remained procedures were performed as disclosed above, except that the anti-rabbit MicroBeads were used. The cells were observed and counted with Leica CTR 4000 fluorescence microscope. The results were shown in FIGS. 7 to 9.

The tissue section of the sham-operated control has very small amount of CD206 expressing M2 phenotype (see FIG. 7). It was found out that the microglia/macrophages activated in the spinal cord injury group express CD206 (M2 macrophage-specific marker) and CD11b (Microglia/macrophage marker) all together as well as ED1 (Activated microglia/macrophage-specific marker) (see FIGS. 7 and 8). Meanwhile, 58.7% of activated microglia/marcophages was CD-206 positive in Substance P-injection group at five days after a spinal cord injury through MACS assay, and the above percentage corresponds to about 6.5 times as compared with the control (see FIG. 9). Accordingly, the results suggest that Substance P induces a conversion of microglia/macrophages into M2 phenotype in a damaged microenvironment.

Example 5

Confirmation of Effect of Decreasing Apoptosis by Substance P—TUNEL Staining and Western Blot Analysis (1) At immediately, 1 d, 2 ds, Substance P or saline (the same volume without Substance P) was injected to a tail vein of rat, using the same method as (1) of Example 1. In order to quantify a degree of apoptosis, the tissues of spinal cords obtained from the experimental group (4 rats/group) and the control (4 rats/group) were longitudinally cut at five days after administration. The tissue section was selected at 1200 μm distant from a ventral surface of spinal cord; then treated with a nerve cell-specific antibody NeuN (1:100, Millipore), oligodendrocyte-specific antibody APC (1:100, Abcam) as a primary antibody; and placed at 4° C. overnight.

Next day, after fully washed with saline, it was treated with a secondary antibody conjugated with cyanine 3 (1:500, Jackson ImmunoResearch) for 1 hour at room temperature. After washed twice with saline, it was stained with in situ cell death detection kit (Fluoresecein, Roche). Vectashield (Vector) including DAPI was covered on a slide, and then was observed with a fluorescence microscope (Leica CTR 4000). In order to confirm and compare a type of cells that surely is in apoptosis from the results of TUNEL positive and DAPI positive staining, only the cells, in which two-staining-overlapped-cells corresponded with NeuN or CD11b positive staining, were shown in FIG. 10.

As shown in FIG. 10, Substance P decreased apoptosis of nerve cells that were mainly caused at one day after damaging or significantly decreased apoptosis of oligodendrocytes at five days after damaging.

(2) Substance P or saline (the same volume without Substance P) was injected to a tail vein of mice, respectively at immediately, 1 d, 2 ds after a spinal cord injury, using the same method as (1) of Example 1. After operating, the experimental group (4 rats/group) and the control (4 rats/group) were sacrificed at one day and five days, respectively. Spinal cord tissues (1 cm) obtained from the animal were homogenized with a dissolution buffer solution (10% glycerol, 20 mM Tris [pH 8.0], 137 mM NaCl, 1% Nonidet P-40, 0.5 mM EDTA, 10 mM $Na_2P_2O_7$, 10 mM NaF, 1 μg/ml aprotinin, 10 μg/ml leupeptin, 1 mM vanadate and 1 mM PMSF). The amounts of proteins in supernatant were determined by using BCA assay (Pierce). The total proteins (50 μg) were isolated through SDS-PAGE, and then transferred to a nitrocellulose (Millipore, Billerica, Mass.) membrane. Then, primary single cell-derived antibodies were treated to the transferred membrane as follows: β-Tubulin (1:10,000; Sigma), Arginase 1 (1:1000; Santa Cruz Biotechnology, Inc., Santa Cruz, Calif.), iNOS (1:10,000; BD Transduction Laboratory, Lexington, Ky.), CD86 (1:1000; BD Transduction Laboratory), cleaved caspase-3 (1:1000; Cell Signaling Technology, Danvers, Mass.). At this time, β-Tubulin was used as an inner comparing group, and each result were determined by performing four independent experiments. The results were shown in FIG. 11.

As shown in FIG. 11, caspase-3 having 19, 17 kD molecular weight was increased up to five days after injuring, and activation of caspase-3 was significantly decreased by administrating Substance P. Accordingly, these results indicate that an administration of Substance P inhibited apoptosis.

Example 6

Confirmation of Effect of Improving Tissue Injury by Substance P after Spinal Cord Injury In order to confirm an effect on neurotrophic factors, Substance P was administrated after a spinal cord injury and then a spinal cord tissue was prepared to perform an immunofluorescence staining, using the same method as (1)-(3) of Example 1. In here, other primary antibodies were use as follows: mouse monoclonal anti-chondroichin sulfate proteoglycan antibody (CSPG, 1:200, Milipore); anti-neurofilament protein 200 kDa antibody (NF200, 1:500, Millipore); rabbit polyclonal anti-CD206 antibody (1:100, Abcam); anti-nerve glial fibrillary acidic protein antibody (GFAP, 1:200, Abcam). The results were shown in FIGS. 12 to 16.

As shown in FIG. 12, it was found that CSPG-positive signal around an injury site was significantly decreased by administrating Substance P and CSPG-positive signal was overlapped to astrocytes at two weeks after spinal cord injury. As reported results, CSPG have an action of inhibiting nerve axon's growth. Additionally, most cells especially astrocytes secrete CSPG at injury site.

As shown in FIG. 13, it was confirmed that CD206 and ED1 double-positive cells were gathered around an injury site in the group that was administrated with Substance P, at two weeks after spinal cord injury. Reversely, at control CD206 and ED1 double-positive cells were presented in smaller amount around injury site. These results demonstrate that CD206 was plentifully presented in Substance P treated group to removing dead cells by combining cells that were in apoptosis and cell necrosis at late-stage, and promotes a regeneration of axone for repairing a tissue. In addition, it was observed that GFAP-positive cells were excluded from CD206-positive spinal cord injury site of Substance P-injected group (see FIG. 14), and a lot of neurofilament proteins were outreached (see FIG. 15). The neurofilament protein was well preserved in Substance P-injected group as compared with the control when exposed to CD206-positive cell field.

Example 7

Confirmation of Effect of Recovering Spinal Cord Nerve by Substance P after Spinal Cord Injury (1) Observation of Ethologic Change An ethologic change test was performed as follows: an experimental animal was put to a large basin having soft and non-smooth bottom (Width 90 cm×Length 130 cm×Height 30 cm); then body's balance states and moving states of hind-leg's coxalgic pelvis, knee joint, and ankle joint were observed when freely walking; then it was converted into a score based on Basso-Bresnahan-Beattie (BBB) locomotor rating scale (Basso et al., 1995); and then four researchers performed a blind technique. Substance P or saline was injected to a tail vein of rat, respectively at immediately, 1 d, 2 d after a spinal cord injury, using the same method as (1) of Example 1. And then, for the experimental group (10 rats/group) and the control (9 rats/group), an ethologic change due to a spinal cord injury was observed and estimated for different periods, such as after injuring, 1 week, 2 weeks, 3 weeks, 4 weeks, 5 weeks, 5 weeks, and 6 weeks. A mean value of scores (BBB scores) observed by four researchers was taken, and the results thereof were statistically analyzed. The results were shown in FIG. 16. The statistical analysis was performed in a method of two-way ANOVA with post hoc Tukey test.

As shown in FIG. 16, it was found that a spinal cord nerve function was beginning to recover from about one week after administrating in the experimental group that was Substance P-injected group as compared with the control. A meaningful improved motor skill was exhibited in Substance P-injected group from 14 days as compared with the control; and a motor skill was meaningfully recovered and improved from about 5 weeks as compared with the control (BBB score experimental group at 6 weeks: 11.5±0.5; Control: 9.3±0.8, P<0.05). These results indicate that through administration of Substance P to treat spinal cord nerve injury acquired improvement of motor skill and functional protection effect was also obtained.

(2) Immunofluorescence Staining

Using the same method as (1)-(3) of Example 1, Substance P was administered after spinal cord injury, spinal cord tissues were prepared, and immunofluorescence staining was performed. in order to investigate as to whether myelin sheath of nerve cell was protected, mouse monoclonal anti-myelin base protein antibody (MBP, 1:50, Santa Cruz Biotechnology), a marker for axone to be re-growth, was used as a primary antibody. The results were shown in FIGS. 17 and 18.

As shown in FIG. 17, it was found that MBP-positive sheath was well preserved in Substance P-injected group, i.e., the experimental group. As shown in FIG. 18, the tissue lose was inhibited up to at least 50% at 2 mm rostal and caudal from the center by administrating Substance P.

REFERENCE DOCUMENTS

Alexianu M E, Kozovska M, Appel S H. Immune reactivity in a mouse model of familial ALS correlates with disease progression. *Neurology.*, 57, 1282 (2001)

Basso D M, Beattie M S, Bresnahan J C., A sensitive and reliable locomotor rating scale for open field testing in rats, *J. Neurotrauma.*, 12, 1 (1995)

Beattie M S., Inflammation and apoptosis: linked therapeutic targets in spinal cord injury, *Trends Mol. Med.*, 10, 580 (2004)

Bracken M B, Shepard M J, Collins W F, et al., A randomized, controlled trial of methylprednisolone or naloxone in the treatment of acute spinal-cord injury. Results of the Second National Acute Spinal Cord Injury Study, *N. Engl. J. Med.*, 322, 1405 (1990)

Chatani K, Kawakami M, Weinstein J N, et al., Characterization of thermal hyperalgesia, c-fos expression, and alterations in neuropeptides after mechanical irritation of the dorsal root ganglion, *SPine.*, 20, 277 (1995)

el Masry W S, Short D J., Current concepts: Spinal injuries and rehabilitation, *Curr Opin Neurol.*, 10, 484 (1997)

Fitch M T, Silver J., CNS injury, glial scars, and inflammation: Inhibitory extracellular matrices and regeneration failure, *Exp Neurol.*, 209, 294 (2008)

Henry J L., Substance P and inflammatory pain: potential of substance P antagonists as analgesics, *Agents Actions Suppl.*, 41, 75 (1993)

Kapoor R, Davies M, Blaker P A, et al., Blockers of sodium and calcium entry protect axons from nitric oxide-mediated degeneration, *Ann Neurol.*, 53, 174 (2003)

Kohlmann O Jr, Cesaretti M L, Ginoza M, et al., Role of substance P in blood pressure regulation in salt-dependent experimental hypertension, Hypertension., 29, 506 (1997)

Kohutnicka M, Lewandowska E, Kurkowska-JastrzebskaI, et al., Microglial and astrocytic involvement in a murine model of Parkinson's disease induced by 1-methyl-4-phenyl-1,2,3,6-tetrahydropyridine (MPTP). *Immunopharmacology.*, 39, 167 (1998)

Kramer M S, Cutler N, Feighner J, et al., Distinct mechanism for antidepressant activity by blockade of central substance P receptors, *Science.*, 281, 1640 (1998)

Liu X Z, Xu X M, Hu R, et al., Neuronal and glial apoptosis after traumatic Spinal cord injury, *J Neurosci.*, 17, 5395 (1997)

Lo E H, Dalkara T, Moskowitz M A., Mechanisms, challenges and opportunities in stroke, *Nat Rev Neurosci.*, 4, 399 (2003)

Lu J, Ashwell K W, Waite P., Advances in secondary Spinal cord injury: role of apoptosis, *Spine.*, 25, 1859 (2000)

Matthay M A, Ware L B., Can nicotine treat sepsis, *Nat. Med.*, 10, 1161 (2004)

Mattson M P, Gleichmann M, Cheng A., Mitochondria in neuroplasticity and neurological disorders, *Neuron.*, 10, 748 (2008)

McGeer P L, McGeer E G. The inflammatory response system of brain: implications for therapy of Alzheimer and other neurodegenerative diseases. *Brain Res Brain Res Rev.*, 21, 195 (1995)

Radhakrishnan V, Henry J L., Electrophysiology of neuropeptides in the sensory Spinal cord, *Prog Brain Res.*, 104, 175 (1995)

Rupniak N M, Kramer M S., Discovery of the anti-depressant and anti-emetic efficacy of substance P receptor (NK1) antagonists. *Trends Pharmacological Sci.*, 20, 485 (1999)

Schwab M E, Bartholdi D., Degeneration and regeneration of axons in the lesion Spinal cord, *Physiol. Rev.*, 76, 319 (1996)

Tansey M G, McCoy M K, Frank-Cannon T C., Neuroinflammatory mechanisms in Parkinson's disease: potential environmental triggers, pathways, and targets for early therapeutic intervention, *Exp Neurol.*, 208, 1 (2007)

Tesco G, Koh Y H, Tanzi R E., Caspase activation increases beta-amyloid generation independently of caspase cleavage of the beta-amyloid precursor protein (APP), *J Biol. Chem.*, 278, 46074 (2003)

Vaught J L., Substance P antagonists and analgesia: a review of the hypothesis, *Life Sci.*, 43, 1419 (1988)

The invention claimed is:

1. A method of treating a traumatic spinal cord injury in a mammal, comprising administering intravenously a composition consisting essentially of Substance P as the active ingredient in a therapeutically effective amount to the mammal in need thereof, wherein the therapeutically effective amount of Substance P is 0.001-0.5 mg/day or 0.0001-0.005 mg/kg.

2. The method of claim 1, wherein the traumatic injury is a flexion injury, a vertical compression injury, a hyperextension injury, or a flexion-rotation injury.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
```

<223> OTHER INFORMATION: TNF-alpha Sense Primer

<400> SEQUENCE: 1
cccagaccct cacactcaga t        21

<210> SEQ ID NO 2
<211> LENGTH: 21
<212> TYPE: DNA
<213> ORGANISM: Artificial Sequence
<220> FEATURE:
<223> OTHER INFORMATION: TNF-alpha Antisense Primer

<400> SEQUENCE: 2
ttgtcccttg aagagaacct g        21

<210> SEQ ID NO 3
<211> LENGTH: 24
<212> TYPE: DNA
<213> ORGANISM: Artificial Sequence
<220> FEATURE:
<223> OTHER INFORMATION: IL-1beta Sense Primer

<400> SEQUENCE: 3
gcagctacct atgtcttgcc cgtg        24

<210> SEQ ID NO 4
<211> LENGTH: 23
<212> TYPE: DNA
<213> ORGANISM: Artificial Sequence
<220> FEATURE:
<223> OTHER INFORMATION: IL-1beta Antisense Primer

<400> SEQUENCE: 4
gtcgttgctt gtctctcctt gta        23

<210> SEQ ID NO 5
<211> LENGTH: 30
<212> TYPE: DNA
<213> ORGANISM: Artificial Sequence
<220> FEATURE:
<223> OTHER INFORMATION: IL-6 Sense Primer

<400> SEQUENCE: 5
aagtttctct ccgcaagata cttccagcca        30

<210> SEQ ID NO 6
<211> LENGTH: 28
<212> TYPE: DNA
<213> ORGANISM: Artificial Sequence
<220> FEATURE:
<223> OTHER INFORMATION: IL-6 Antisense Primer

<400> SEQUENCE: 6
aggcaaattt cctggttata tccagttt        28

<210> SEQ ID NO 7
<211> LENGTH: 22
<212> TYPE: DNA
<213> ORGANISM: Artificial Sequence
<220> FEATURE:
<223> OTHER INFORMATION: iNOS Sense Primer

<400> SEQUENCE: 7
ctccatgact ctcagcacag ag        22

-continued

```
<210> SEQ ID NO 8
<211> LENGTH: 22
<212> TYPE: DNA
<213> ORGANISM: Artificial Sequence
<220> FEATURE:
<223> OTHER INFORMATION: iNOS Antisense Primer

<400> SEQUENCE: 8
gcaccgaaga tatcctcatg at                                              22

<210> SEQ ID NO 9
<211> LENGTH: 23
<212> TYPE: DNA
<213> ORGANISM: Artificial Sequence
<220> FEATURE:
<223> OTHER INFORMATION: IL-10 Sense Primer

<400> SEQUENCE: 9
gagtgttcaa agggaaatta tat                                             23

<210> SEQ ID NO 10
<211> LENGTH: 20
<212> TYPE: DNA
<213> ORGANISM: Artificial Sequence
<220> FEATURE:
<223> OTHER INFORMATION: IL-10 Antisense Primer

<400> SEQUENCE: 10
ctggtttctc ttcccaagac                                                 20

<210> SEQ ID NO 11
<211> LENGTH: 24
<212> TYPE: DNA
<213> ORGANISM: Artificial Sequence
<220> FEATURE:
<223> OTHER INFORMATION: TGF-beta Sense Primer

<400> SEQUENCE: 11
gagagccctg gataccaact actg                                            24

<210> SEQ ID NO 12
<211> LENGTH: 24
<212> TYPE: DNA
<213> ORGANISM: Artificial Sequence
<220> FEATURE:
<223> OTHER INFORMATION: TGF-beta Antisense Primer

<400> SEQUENCE: 12
ctccaccttg ggcttgcgac ccac                                            24

<210> SEQ ID NO 13
<211> LENGTH: 22
<212> TYPE: DNA
<213> ORGANISM: Artificial Sequence
<220> FEATURE:
<223> OTHER INFORMATION: Beta-actin Sense Primer

<400> SEQUENCE: 13
cttctgcatc ctgtcaggat gc                                              22

<210> SEQ ID NO 14
<211> LENGTH: 24
<212> TYPE: DNA
<213> ORGANISM: Artificial Sequence
<220> FEATURE:
<223> OTHER INFORMATION: Beta-actin Antisense Primer
```

-continued

```
<400> SEQUENCE: 14
agaagagcta tgagctgcct gacg                                              24
```